United States Patent
Liu et al.

(10) Patent No.: US 11,684,951 B2
(45) Date of Patent: Jun. 27, 2023

(54) MICROMACHINED ULTRASONIC TRANSDUCER DEVICES HAVING TRUNCATED CIRCLE SHAPED CAVITIES

(71) Applicant: BFLY OPERATIONS, INC., Burlington, MA (US)

(72) Inventors: Jianwei Liu, Fremont, CA (US); Lingyun Miao, Fremont, CA (US); Sarp Satir, San Francisco, CA (US)

(73) Assignee: BFLY OPERATIONS, INC., Burlington, MA (US)

( * ) Notice: Subject to any disclaimer, the term of this patent is extended or adjusted under 35 U.S.C. 154(b) by 199 days.

(21) Appl. No.: 16/988,125

(22) Filed: Aug. 7, 2020

(65) Prior Publication Data
US 2021/0038193 A1    Feb. 11, 2021

Related U.S. Application Data

(60) Provisional application No. 62/884,569, filed on Aug. 8, 2019.

(51) Int. Cl.
| | | |
|---|---|---|
| *B06B 1/02* | (2006.01) | |
| *H04R 31/00* | (2006.01) | |
| *A61B 8/00* | (2006.01) | |
| *B06B 1/06* | (2006.01) | |

(52) U.S. Cl.
CPC .......... *B06B 1/0292* (2013.01); *A61B 8/4494* (2013.01); *H04R 31/006* (2013.01); *B06B 1/0629* (2013.01)

(58) Field of Classification Search
CPC ....... A61B 8/4494; A61B 8/4483; A61B 8/44; A61B 8/4444; A61B 8/4488; B06B 1/0607; B06B 1/0292; B06B 2201/55; H04R 31/006; H04R 17/00; B81C 1/00182
See application file for complete search history.

(56) References Cited

U.S. PATENT DOCUMENTS

| | | |
|---|---|---|
| 9,067,779 B1 | 6/2015 | Rothberg et al. |
| 9,499,392 B2 | 11/2016 | Rothberg et al. |
| 9,521,991 B2 | 12/2016 | Rothberg et al. |
| 9,533,873 B2 | 1/2017 | Rothberg et al. |
| 9,592,030 B2 | 3/2017 | Rothberg et al. |
| 10,272,471 B2 | 4/2019 | Alie et al. |

(Continued)

FOREIGN PATENT DOCUMENTS

WO    WO 2017/222964 A1    12/2017

OTHER PUBLICATIONS

International Search Report and Written Opinion dated Apr. 30, 2020 in connection with International Application No. PCT/US2020/017013.

(Continued)

*Primary Examiner* — Sean D Mattson
*Assistant Examiner* — Michael Yiming Fang
(74) *Attorney, Agent, or Firm* — Osha Bergman Watanabe & Burton LLP

(57) ABSTRACT

An ultrasonic transducer device is provided. In some embodiments, the ultrasonic transducer device includes a substrate having a membrane support layer formed on a bottom cavity layer, and an opening in the membrane support layer so as to form a transducer cavity. In some embodiments, the opening comprises a truncated circle shape.

12 Claims, 10 Drawing Sheets

(56) References Cited

U.S. PATENT DOCUMENTS

| | | |
|---|---|---|
| 10,497,856 B2 | 12/2019 | Rothberg et al. |
| 2003/0011283 A1 | 1/2003 | Takeuchi et al. |
| 2008/0042225 A1 | 2/2008 | Machida et al. |
| 2011/0055447 A1 | 3/2011 | Costa |
| 2014/0217478 A1 | 8/2014 | Rothberg et al. |
| 2014/0264660 A1 | 9/2014 | Rothberg et al. |
| 2014/0332911 A1 | 11/2014 | Dirksen et al. |
| 2017/0291192 A1* | 10/2017 | Machida ............... B06B 1/0644 |
| 2017/0365774 A1* | 12/2017 | Rothberg ............... H01L 41/047 |
| 2019/0231312 A1 | 8/2019 | Fife et al. |
| 2019/0275561 A1 | 9/2019 | Fife et al. |
| 2019/0336099 A1 | 11/2019 | Fife et al. |
| 2019/0336103 A1 | 11/2019 | Fife et al. |
| 2019/0336104 A1 | 11/2019 | Fife et al. |
| 2020/0013691 A1 | 1/2020 | Liu et al. |
| 2020/0061670 A1* | 2/2020 | Chan ..................... B06B 1/0622 |
| 2020/0102214 A1 | 4/2020 | Liu et al. |
| 2020/0147641 A1 | 5/2020 | Fife et al. |
| 2020/0156110 A1 | 5/2020 | Miao et al. |
| 2020/0171538 A1* | 6/2020 | Takezaki ............. G01N 29/2406 |
| 2020/0254487 A1 | 8/2020 | Miao et al. |
| 2021/0043826 A1* | 2/2021 | Ghyselen ............... B06B 1/0292 |
| 2021/0169445 A1* | 6/2021 | Weekemp ............. A61B 8/4494 |
| 2021/0393238 A1* | 12/2021 | Guma ................... A61B 8/4272 |

OTHER PUBLICATIONS

Daft et al., Microfabricated ultrasonic transducers monolithically integrated with high voltage electronics. Proc Ultrason Symp. 2004;493-6.

Gurun et al., Front-end CMOS electronics for monolithic integration with CMUT arrays: circuit design and initial experimental results. Proc Ultrason Symp. 2008;390-3.

Kupnik et al., CMUT Fabrication Based On A Thick Buried Oxide Layer. Proc IEEE Ultrason Symp. Oct. 2010;2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 21, 2010;1-22.

* cited by examiner

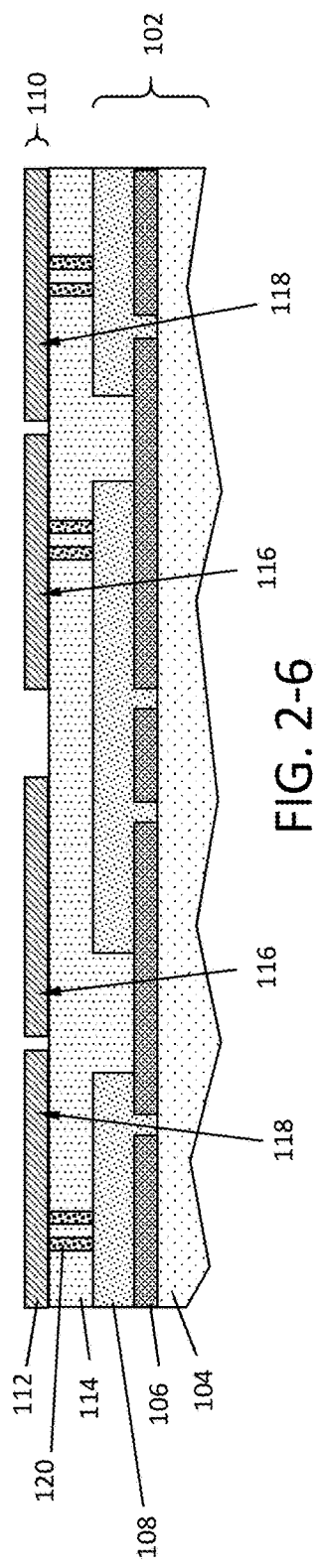
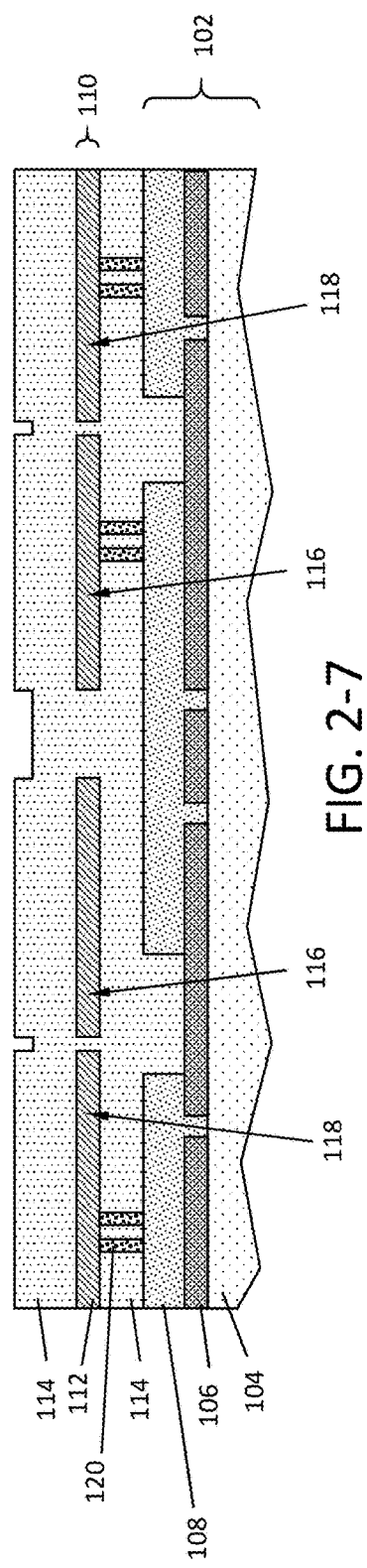
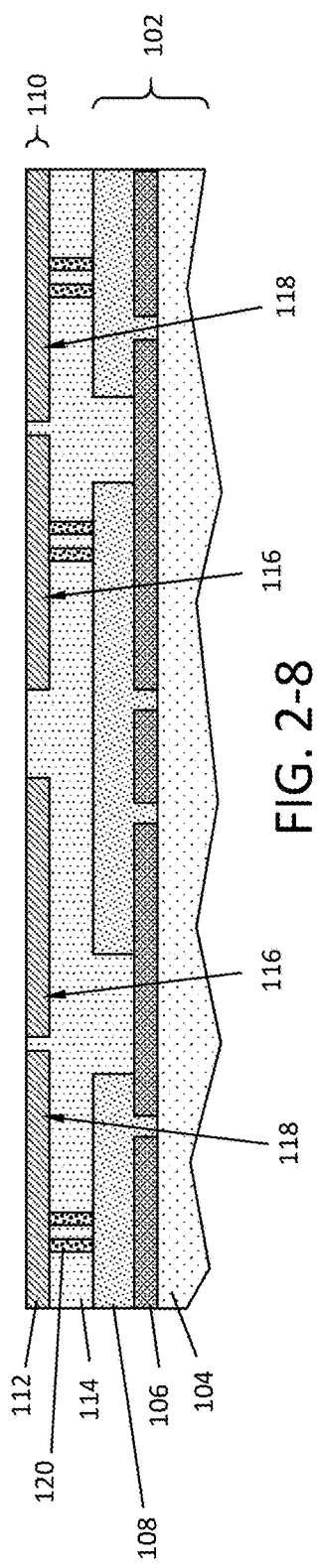
FIG. 2-6
FIG. 2-7
FIG. 2-8

MICROMACHINED ULTRASONIC TRANSDUCER DEVICES HAVING TRUNCATED CIRCLE SHAPED CAVITIES

CROSS-REFERENCE TO RELATED APPLICATIONS

This application claims the benefit under 35 U.S.C. § 119(e) of U.S. Patent Application Ser. No. 62/884,569, filed Aug. 8, 2019 under B1348.70154US00, and entitled "MICROMACHINED ULTRASONIC TRANSDUCER DEVICES HAVING TRUNCATED CIRCLE SHAPED CAVITIES," which is hereby incorporated by reference herein in its entirety.

BACKGROUND

The present disclosure relates generally to micromachined ultrasonic transducers and, more specifically, to micromachined ultrasonic transducer devices having truncated circle shaped cavities.

Ultrasound devices may be used to perform diagnostic imaging and/or treatment, using sound waves with frequencies that are higher than those audible to humans. When pulses of ultrasound are transmitted into tissue, sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound images.

Some ultrasound imaging devices may be fabricated using micromachined ultrasonic transducers, including a flexible membrane suspended above a substrate. A cavity is located between part of the substrate and the membrane, such that the combination of the substrate, cavity and membrane form a variable capacitor. When actuated by an appropriate electrical signal, the membrane generates an ultrasound signal by vibration. In response to receiving an ultrasound signal, the membrane is caused to vibrate and, as a result, generates an output electrical signal.

SUMMARY

According to an aspect of the present application, an ultrasonic transducer device is provided, including a substrate having a membrane support layer formed on a bottom cavity layer, and an opening in the membrane support layer so as to form a transducer cavity. In some embodiments, the opening comprises a truncated circle shape.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 2-1 through 2-11 are a series of cross-sectional views illustrating a process that may be used to form the transducer device of FIG. 1.

FIG. 3 is a plan view of a portion of a transducer array having completely circular shaped transducer cavities.

FIG. 4 is a plan view of a portion of a transducer array having truncated circular shaped transducer cavities, in accordance with an exemplary embodiment.

FIG. 5 is another plan view of a portion of the transducer array of FIG. 4, and more specifically illustrating an exemplary patterning arrangement of the transducer bottom electrode layer within the cavity footprint.

FIG. 6 is a graph illustrating exemplary acoustic performance of a circular transducer cavity such as in FIG. 3.

FIG. 7 is a graph illustrating exemplary acoustic performance of a truncated circular transducer cavity such as in FIG. 4.

FIG. 8 is a top view of an example ultrasonic transducer device that may be formed using the truncated circular shaped transducer cavities of FIG. 4 and FIG. 5.

DETAILED DESCRIPTION

The techniques and structures described herein relate to micromachined ultrasonic transducer devices having truncated circle shaped cavities for improved cavity bonding operations in the manufacturing of micromachined ultrasonic transducer (MUT) cavities. In one aspect, a truncated circle shaped transducer cavity provides additional surface area for transducer membrane bonding (with respect to a completely circular cavity shape), specifically at the narrowest local bonding regions adjacent and between "nearest neighbor" transducers, and without a substantial drop off in transducer acoustic performance as compared to a completely circular transducer geometry. Accordingly, a low temperature oxide bonding process margin may be improved with the transducer acoustic response being minimally affected by the modified cavity geometry.

One type of transducer suitable for use in ultrasound imaging devices is a MUT, which can be fabricated from, for example, silicon and configured to transmit and receive ultrasound energy. MUTs may include capacitive micromachined ultrasonic transducers (CMUTs) and piezoelectric micromachined ultrasonic transducers (PMUTs), both of which can offer several advantages over more conventional transducer designs such as, for example, lower manufacturing costs and fabrication times and/or increased frequency bandwidth. With respect to the CMUT device, the basic structure is a parallel plate capacitor with a rigid bottom electrode and a top electrode residing on or within a flexible membrane. Thus, a cavity is defined between the bottom and top electrodes. In some designs (such as those produced by the assignee of the present application for example), a CMUT may be directly integrated on an integrated circuit that controls the operation of the transducer. One way of manufacturing a CMUT is to bond a membrane substrate to an integrated circuit substrate, such as a complementary metal oxide semiconductor (CMOS) substrate. This may be performed at temperatures sufficiently low to prevent damage to the devices of the integrated circuit.

Figure 1:
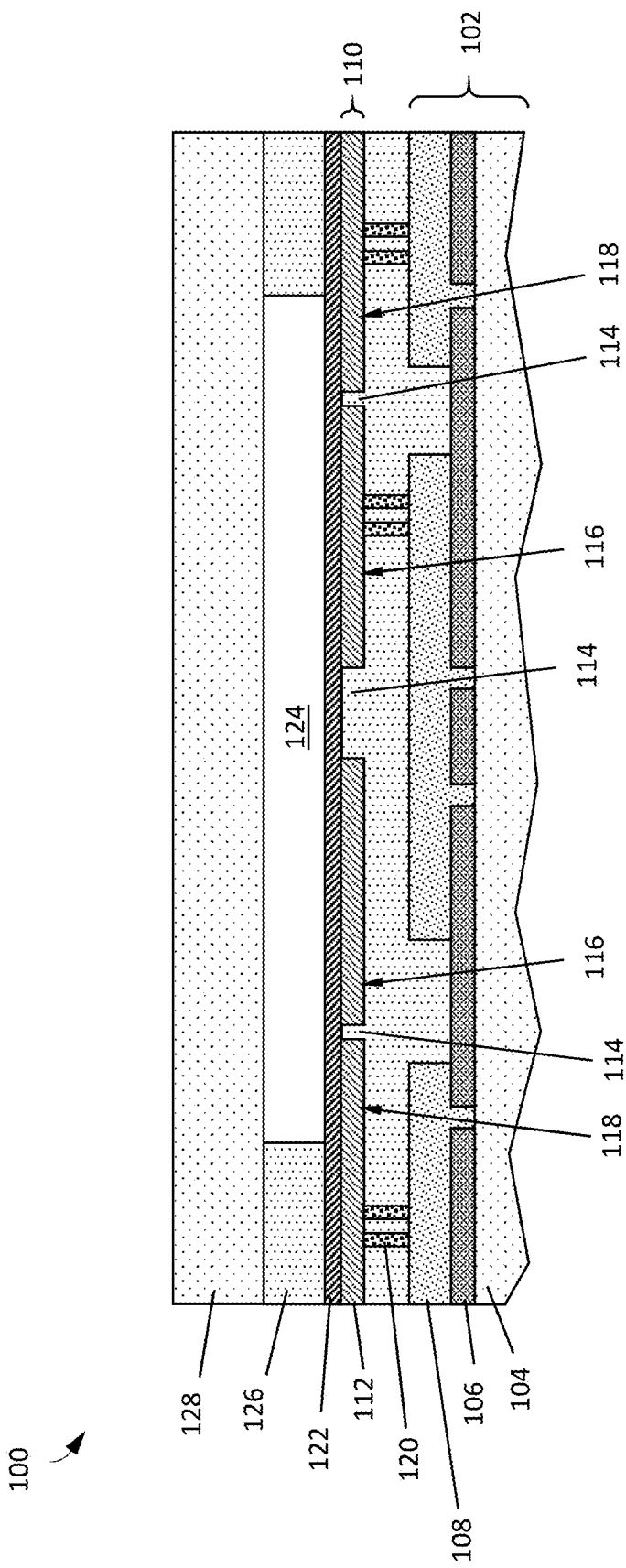
FIG. 1 is a cross-sectional view of an exemplary micromachined ultrasonic transducer device.

Referring initially now to FIG. 1, there is shown a cross-sectional view of an exemplary micromachined ultrasonic transducer device 100, such as a CMUT. The transducer device 100 includes a substrate, generally designated by 102, (e.g., a CMOS substrate, such as silicon) having one or more layers, such as for example: CMOS integrated circuits and wiring layers (at or below region 104), one more insulation/passivation layers 106, and one or more wiring redistribution layers 108. A transducer bottom electrode layer, designated generally at 110, is disposed over the substrate 102 and includes patterned regions of a metal layer 112 (e.g., titanium (Ti)), between which are located regions of an insulation layer 114 (e.g., SiO$_2$). In the illustrated example, first portions of the patterned metal layer 112 may serve as a transducer bottom electrode 116 (e.g., in a "donut" or ring configuration), while second portions of the patterned metal layer 112 may serve another function (e.g., a bypass metal structure 118). As specific substrate and transducer bottom electrode patterns are not the focus of the present disclosure, only a single example is presented in the figures. It will be appreciated, however, that the present embodiments may also be implemented in conjunction with several other transducer electrode structures including (but not limited to), for example: the aforementioned donut shaped electrode pattern (e.g., interior metal removed), multiple segment or ring electrodes, and additional metal patterns used for other purposes besides bottom electrodes (e.g., cavity getter during bonding).

Still referring to FIG. 1, electrically conductive vias 120 (e.g., tungsten (W)) electrically connect the one or more wiring redistribution layers 108 to the patterned metal layer 112 of the transducer bottom electrode layer 110. The formation and specific locations of such vias 120 is discussed in further detail below. A bottom cavity layer 122 is disposed over the transducer bottom electrode layer 110. The bottom cavity layer 122 may include, for example, a thin film layer stack including an SiO$_2$ layer deposited by chemical vapor deposition (CVD) and an aluminum oxide (Al$_2$O$_3$) layer deposited by atomic layer deposition (ALD). A transducer cavity 124 is defined by lithographic patterning and etching of a membrane support layer 126 that is formed on the bottom cavity layer 122. The membrane support layer 126 may be an insulating layer, such as SiO$_2$ for example, the remaining portions of which provide a support surface to which a flexible transducer membrane 128 (e.g., highly doped silicon at a concentration of about $1\times10^{18}$ atoms/cm$^3$ to about $1\times10^{19}$ atoms/cm$^3$) is bonded.

In order to preserve the integrity and functionality of the various CMOS devices residing within the substrate 102 (such as CMOS circuits and wiring layers at or below region 104), a relatively low temperature bonding process (e.g., less than about 450° C.) is employed for bonding the transducer membrane 128 to the membrane support layer 126. Accordingly, it is desirable to have a smooth bonding interface between the bonded surfaces. In one example, a surface roughness less than about 1 nanometers (nm) over a range of 100 microns (m) may be desirable for this purpose. Thus, chemical mechanical polishing (CMP) may be used during the manufacturing process to planarize certain structures such as the metal layer 112, the insulation layer 114, and the material (e.g., W) of the vias 120 in order to provide a smooth bonding interface for downstream steps.

Figures 1, 2:
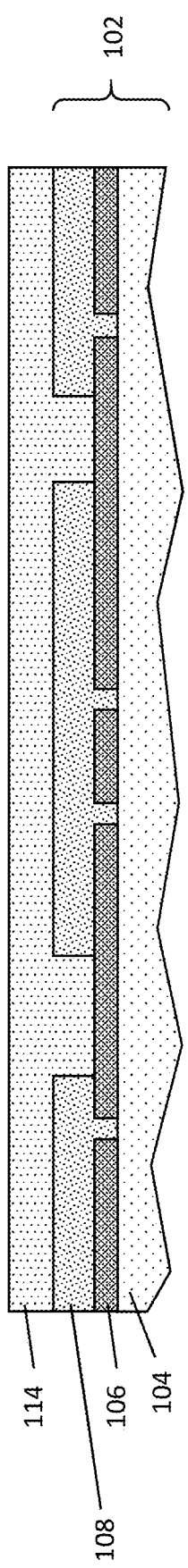
Figure 2:
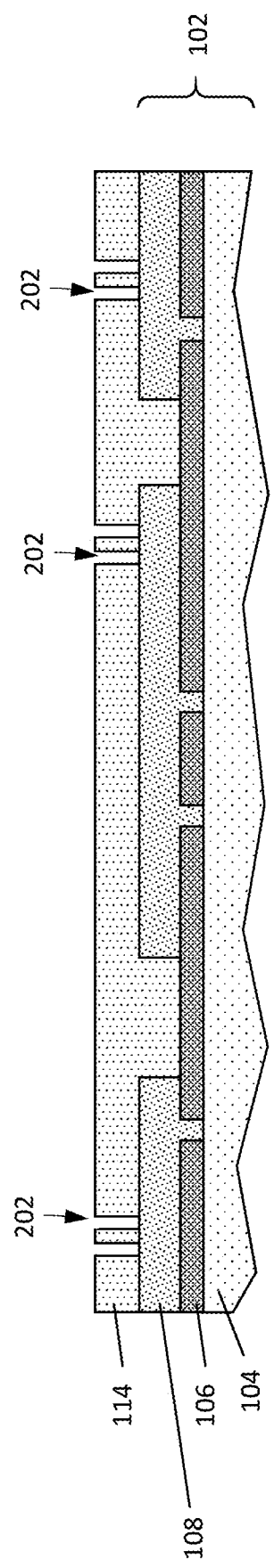
Figures 2, 3:
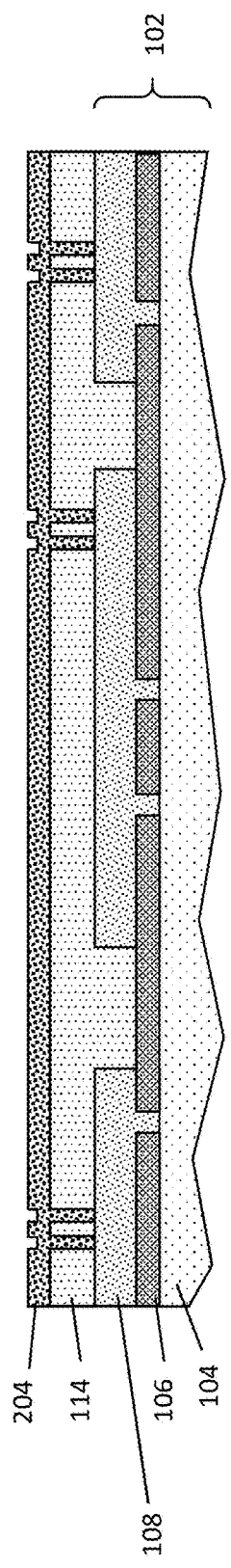
Figures 2, 3, 4:
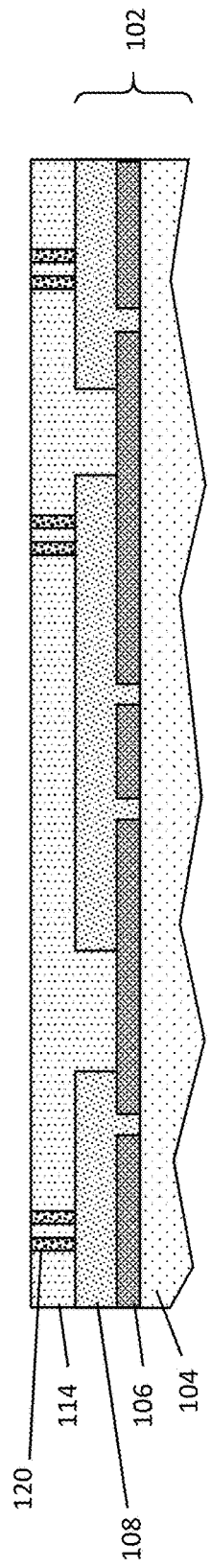

By way of further illustration, FIGS. 2-1 through 2-10 are a series of cross-sectional views illustrating a process that may be used to form the transducer device of FIG. 1 and, more specifically, the aforementioned vias 120 connecting the one or more wiring redistribution layers 108 to the transducer bottom electrode layer 110. FIG. 2-1 illustrates the CMOS substrate 102 having insulation layer 114 formed thereon. In FIG. 2-2, via openings 202 are patterned into the insulation layer using, for example a patterned photoresist material (not shown) followed by etching to access the one or more wiring redistribution layers 108. Then, as shown in FIG. 2-3, a fill material metal layer 204 such as W, for example, is formed over the patterned insulation layer 114 and via openings 202. This is followed by a planarizing operation, such as chemical mechanical polishing (CMP) for example, to remove excess fill material of the metal layer 204 to the top surface of the insulation layer 114, thereby defining the vias as shown in FIG. 2-4.

In FIG. 2-5, the metal layer 112 (e.g., Ti) defining the bottom electrode layer 110 is deposited. The metal layer 112 is patterned as shown in FIG. 2-6 (such as by photoresist patterning and etching) to define the aforementioned transducer electrode and bypass metal structures 116, 118, respectively. This is followed by deposition of additional oxide material fill (e.g., the same as insulation layer 114) as shown in FIG. 2-7 and oxide planarizing as shown in FIG. 2-8. Then, in FIG. 2-9, the membrane support layer 126 is formed, followed by etching of the transducer cavity 124 in FIG. 2-10. The transducer cavity 124 may then be sealed by bonding a transducer membrane 128 to the membrane support layer 126 as illustrated in FIG. 2-11. Such a bonding operation may be, for example, a low temperature oxide-to-oxide fusing bonding process in which the transducer membrane 128 is bonded to the membrane support layer 126 at about room temperature and thereafter annealed at a temperature below about 450° C.

One of the key challenges in maintaining desired bonding integrity at such relatively low temperatures (to in turn protect CMOS circuit integrity) is to achieve a very smooth bonding interface. In the example described, the bonding interface is represented by the top surface of the membrane support layer 126 and the bottom surface of the transducer membrane 128. Such an interface desirably has a surface roughness of less than about 1 nm over a range of about 100 µm. In addition, reliable low temperature bonding is facilitated by having a certain minimum ratio of the total wafer bonding area to the entire wafer area, both globally and locally. For example, it may be desirable to have the percentage of the total bonding area normalized to the entire wafer area be at least 50%, as well as to avoid very small features/dimensions of wafer material from being bonded (e.g., greater than about 10 µm in the minimum dimension). Therefore, efforts should be made in parallel to both produce a high-quality bonding surface, as well as to increase the bonding ratio if possible.

Accordingly, the inventors herein have recognized that a modified transducer cavity shape, such as a truncated circle for example, provides for increased bonding area with respect to completely circular shaped cavities, particularly at the narrowest local bonding patterns. Consequently, a low temperature oxide bonding process margin may be improved. Furthermore, as described in further detail herein, simulation results have demonstrated that the proposed cavity geometry modifications and associated bonding improvements come without any substantial decrease or penalty in transducer acoustic performance.

By way of further illustration, FIG. 3 is a plan view of a portion of a transducer array having completely circular shaped transducer cavities 300. The circular shaped cavities 300 may be similar to the cavity 124 of the transducer device 100 of FIG. 1. It should be appreciated that although there are only four cavities 300 depicted in FIG. 3, a functional transducer device may have many more individual cavities (e.g., hundreds, thousands, tens of thousands, hundreds of thousands, etc.). In any case, the transducer cavities 300 of FIG. 3 are disposed at a certain pitch, p, in both x and y directions and are spaced apart from a nearest neighbor cavity 300 by a distance, d. On one hand, it is desirable to be able to increase the number of individual transducers within a given device region/area to enhance performance, but on the other hand this also means the bonding ratio decreases. For example, the distance d between transducer cavities 300 may be, for example, on the order of about 10-12 µm. One way to increase the bonding ratio using the same circular cavity geometry may be to increase the spacing distance d, but with the tradeoff of increasing the pitch p, and therefore decreasing the total number of transducers within the given device area.

Accordingly, FIG. 4 is a plan view of a portion of a transducer array having truncated circle shaped transducer cavities 400, in accordance with an embodiment. In the example depicted, the truncated circle shaped transducer cavities 400 are spaced at a same pitch p with respect to the circular transducer cavities 300 in FIG. 3, but with an increased nearest neighbor distance of about 2 d, which increases the wafer bonding ratio without reducing the number of transducer elements within the given device area. As illustrated in FIG. 4, one way to realize a truncated circle geometry for the transducer cavities 400 may be to modify a completely circular geometry (shown in dashed lines) with straight edges 402 at nearest neighbor locations. The rest of the cavity geometry may be circular, as indicated by circular portions 404. The straight edges 402 define chords of a circle, and can have a length so as to cut off a sufficient portion of the circular geometry such that the nearest neighbor distance between adjacent transducer cells is at a desirable distance for bonding purposes, such as 2 d for example, with respect to the completely circular configuration of FIG. 3. That is, the truncated edges may be shaped so as to effectively increase the distance between the neighboring transducer cavities. The increase may amount approximately to a doubling of the distance. Thus, if d in FIG. 3 is about 10-15 µm, then 2 d in FIG. 4 may be about 20-30 µm.

Although the exemplary transducer cavity geometry of FIG. 4 may not significantly increase the overall bonding area (i.e., the global bonding ratio), the local bonding ratio may be significantly enhanced. Thus, a truncated circle shape cavity design may allow for more process margin for a low temperature oxide-to-oxide fusion bonding, and in turn facilitate volume production of such devices.

It should be appreciated that, in the context of the present application, the term "truncated circle" generally refers to a plane figure or shape generated by separating four quarters of a circle (e.g., 404) and connecting their ends with straight lines (e.g., 402). However, it is also contemplated within the scope of the present embodiments that the term "truncated circle" may also describe similar geometric structures such as "rounded squares" or "squircles." A "squircle" is a portmanteau of square and circle, and describes a mathematical shape intermediate between a square and a circle, such as four substantially linear sides connected with substantially semi-circular rounded corners. Still other terminology (e.g., "chamfered edges") may be used to describe such geometry while falling under the scope of the present embodiments.

Figures 2, 3, 4, 5:
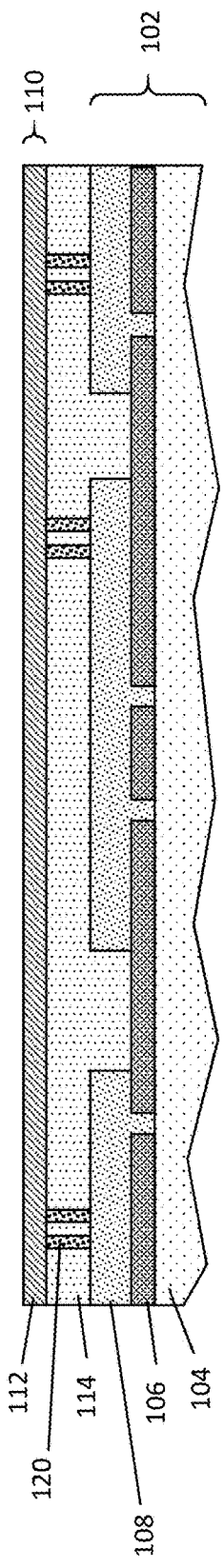

Referring now to FIG. 5, there is shown another plan view of a portion of the transducer array of FIG. 4, and more specifically illustrating an exemplary patterning arrangement of the transducer bottom electrode layer 110 as viewed from within the cavity footprint. In the embodiment illustrated, the transducer electrode structure 116 is patterned as a circular shaped "donut" with insulation layer 114 disposed at the center, and the bypass metal structure 118 corresponding to the cavity location assuming the truncated circle geometry with straight edges 402.

Figures 2, 3, 4, 5, 6, 7, 8, 9:
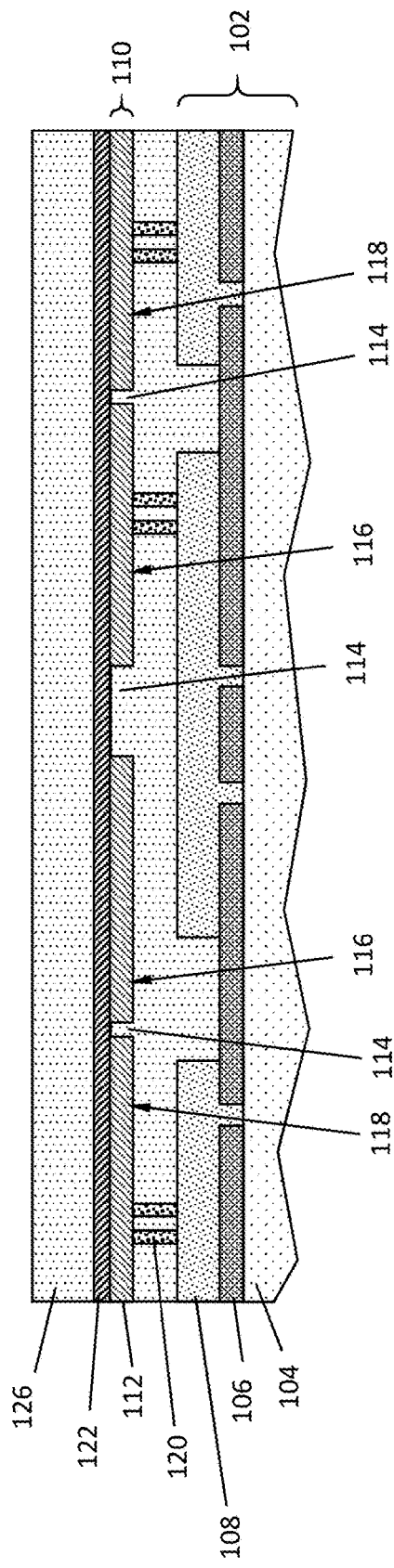
Figures 2, 3, 4, 5, 6, 7, 8, 9, 10:
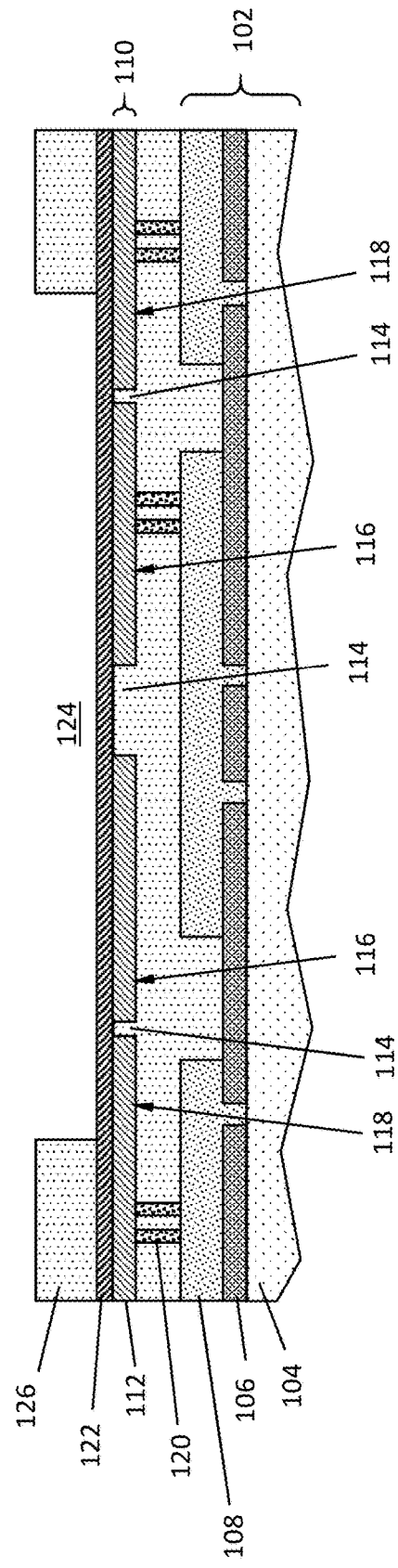
Figures 2, 3, 4, 5, 6, 7, 8, 9, 10, 11:
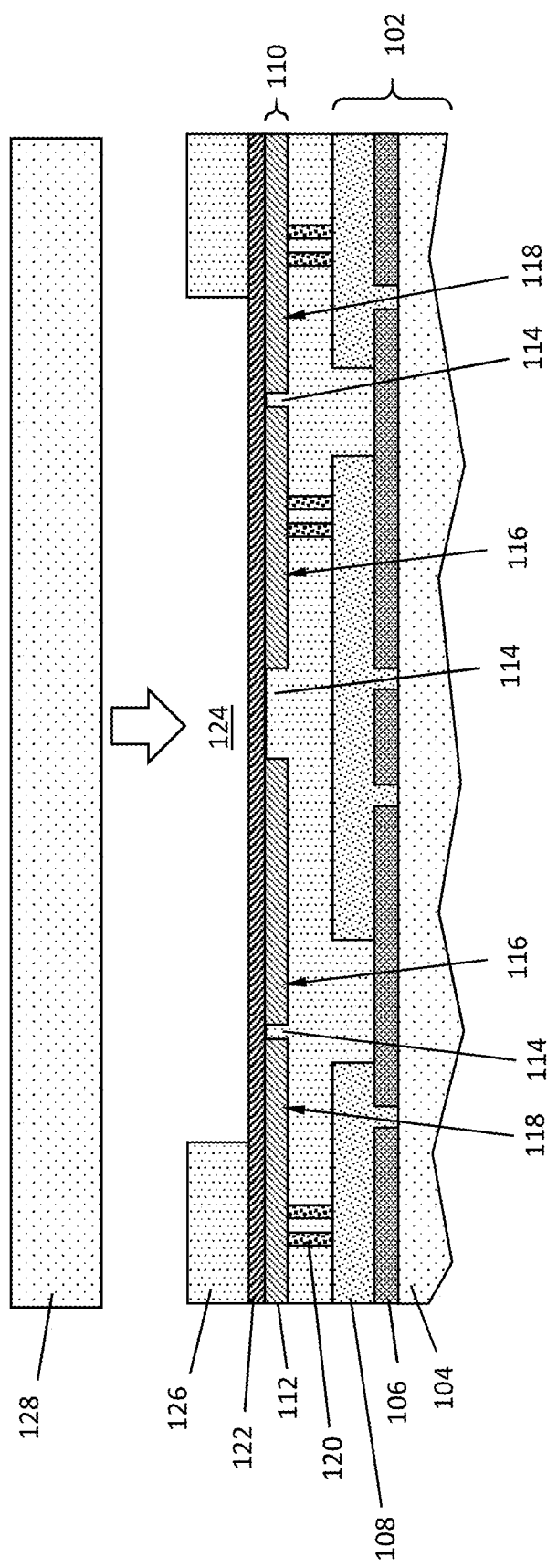
Figure 4:
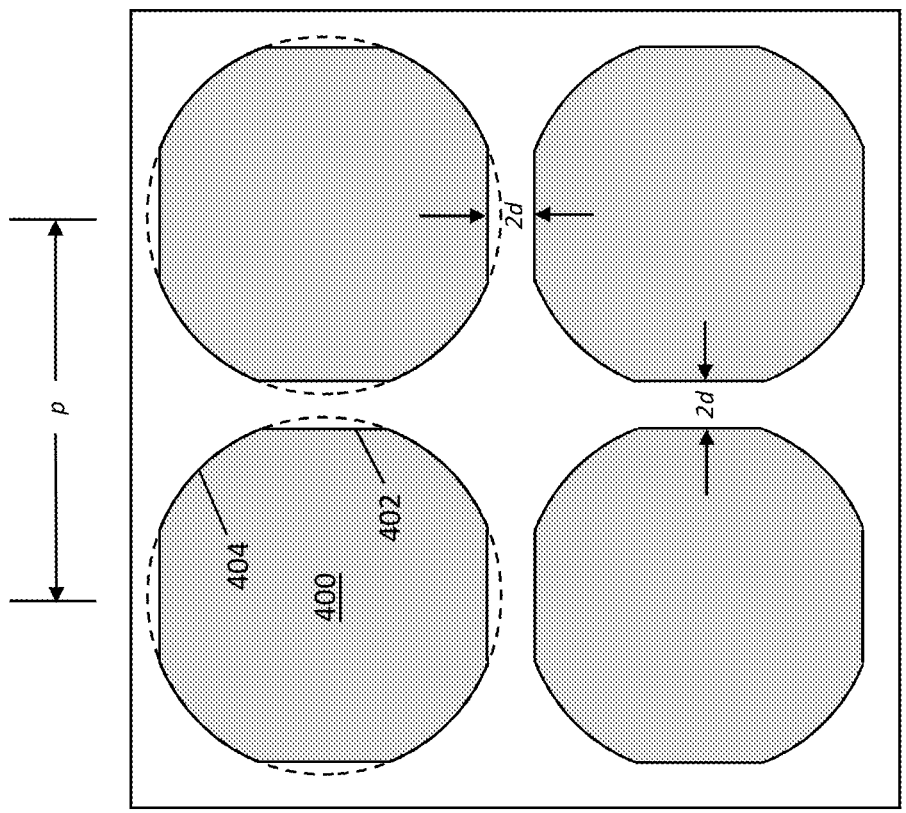
Figure 3:
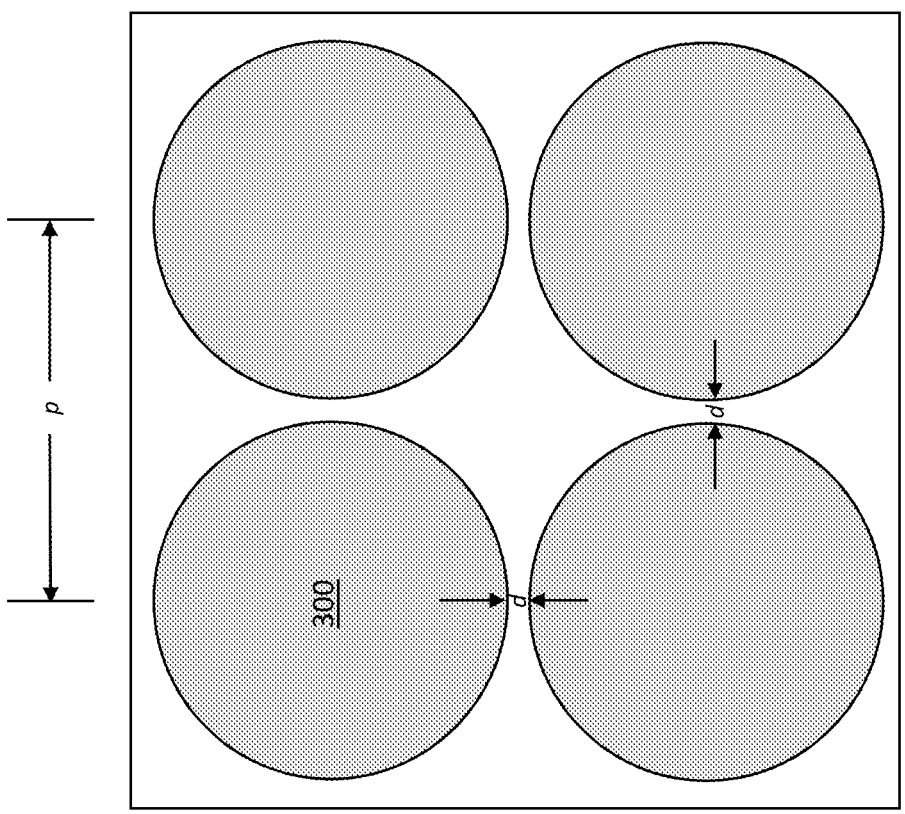
Figure 5:
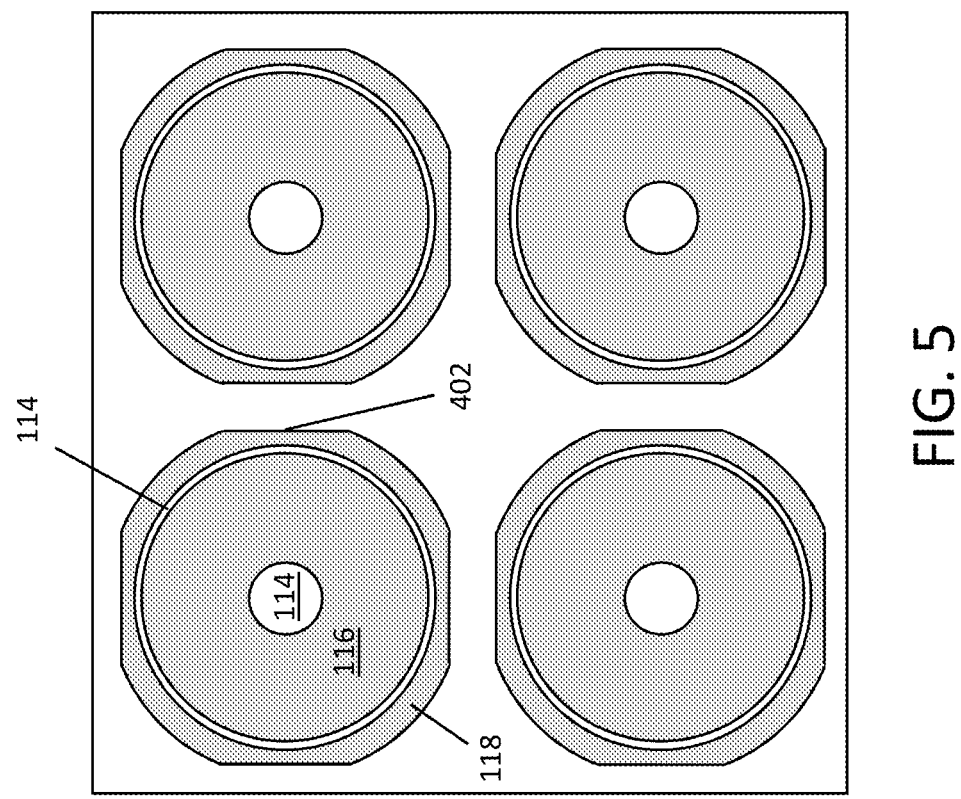
Figure 6:
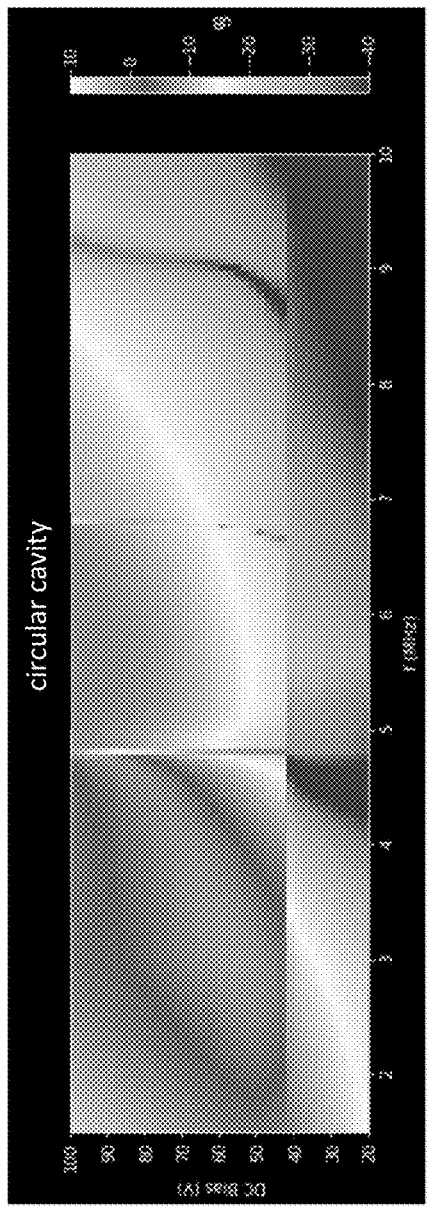
Figure 7:
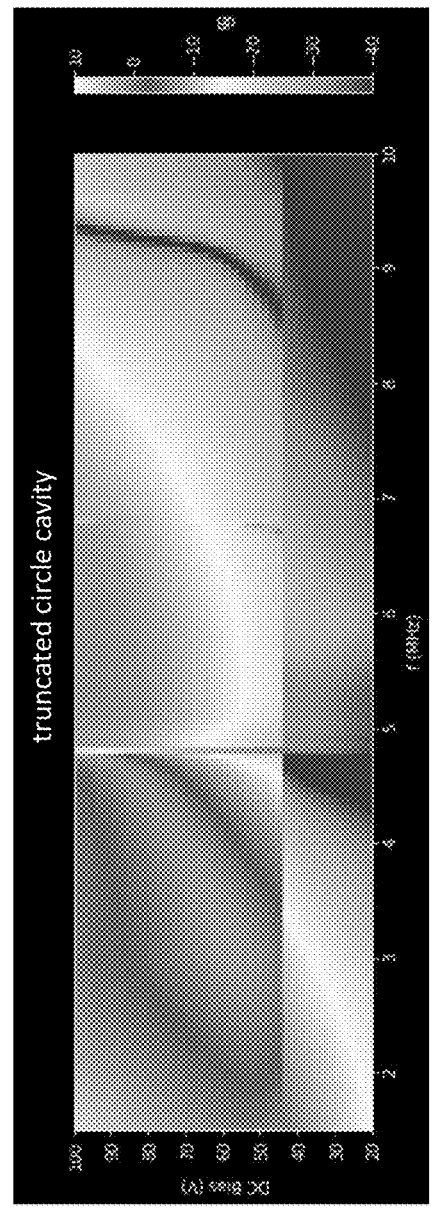
Figure 8:
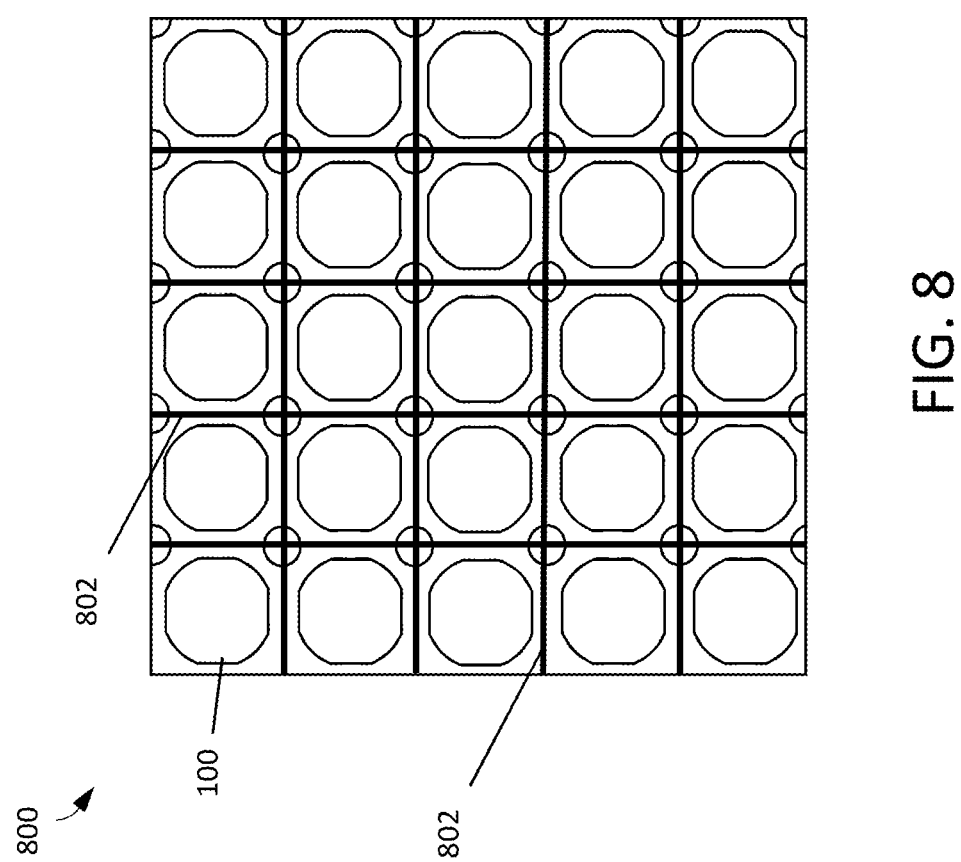

As indicated above, the proposed truncated circle shaped cavity geometry design may offer bonding improvements, and without any significant decrease or penalty in transducer acoustic performance. This may be illustrated by a comparison of the graphs illustrated in FIG. 6 and FIG. 7. More specifically, FIG. 6 is a graph illustrating exemplary acoustic performance of a circular transducer cavity such as the cavity 300 in FIG. 3, and FIG. 7 is a graph illustrating exemplary acoustic performance of a truncated circular transducer cavity such as the cavity 400 in FIG. 4. The graphs illustrate acoustic sensing sensitivity (measured in dB) as a function of transducer DC bias voltage and over a range of operating frequencies. As can be seen in the comparison between FIG. 6 and FIG. 7, there is an almost imperceptible difference in the truncated circle shaped cavity transducer performance, except for a slight reduction in gain at DC bias voltages above 50 V in the operating frequency around 9 MHz.

FIG. 8 illustrates a top view of an example ultrasonic transducer device 800 that may be formed using the truncated circular shaped transducer cavities of FIG. 4 and FIG. 5. As illustrated, the transducer device includes an array of individual transducers 100, such as those respectively described above in conjunction with FIGS. 1-5. The specific number of transducers 100 shown in FIG. 8 should not be construed in any limiting sense, and may include any number suitable for a desired imaging application, which may be for example on the order of tens, hundreds, thousands, tens of thousands or more. FIG. 8 further illustrates an example location of metal 802 that may distribute an electrical signal to the membranes (upper electrodes) of the transducers 100.

As will thus be appreciated, the above described embodiments, whether implemented alone or in combination with one another, may provide certain benefits such as (for example) improved process margins and wafer bonding yield. As such, they may be particularly desirable for volume manufacturing of ultrasonic transducer devices and systems incorporating such devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, some aspects of the technology may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasonic transducer device, comprising:
a substrate having a membrane support layer formed on a bottom cavity layer;
an opening in the membrane support layer so as to form a transducer cavity, wherein the opening comprises a squircle shape; and
a plurality of openings in the membrane support layer so as to form a plurality of transducer cavities; wherein:
the transducer cavity is a first transducer cavity, the squircle shape of the first transducer cavity comprises a first linear side corresponding to a location adjacent a second linear side of a squircle shape of a second transducer cavity of the plurality of transducer cavities, and the second transducer cavity is a nearest neighbor of the first transducer cavity; and
the first linear side of the first transducer cavity and the second linear side of the second transducer cavity are shaped so as to double a nearest neighbor distance between the first transducer cavity and the second transducer cavity compared to the nearest neighbor distance if the openings of the first and second transducer cavities comprised circle shapes centered at same locations as the squircle shapes of the first and second transducer cavities and having a same radius of curvature as curved portions of the squircle shapes of the first and second transducer cavities.

2. The device of claim 1, wherein each of the plurality of transducer cavities has four (4) truncated edges.

3. The device of claim 1, wherein a distance between the first linear side of the first transducer cavity and the second linear side of the second transducer cavity is 20-30 microns (μm).

4. The device of claim 1, wherein a minimum distance between any of the plurality of transducer cavities is at least 10 μm.

5. The device of claim 1, further comprising a transducer membrane bonded to the membrane support layer so as to seal the plurality of transducer cavities.

6. The device of claim 5, wherein a bond between the transducer membrane and the membrane support layer defines a bonding area, and wherein a percentage of the bonding area normalized to an entire wafer area of the ultrasonic transducer device is at least 50%.

7. The device of claim 5, wherein the sealed transducer cavities define capacitive micromachined ultrasonic transducers (CMUTs).

8. The device of claim 7, wherein the membrane support layer comprises $SiO_2$.

9. The device of claim 8, wherein the transducer membrane is flexible.

10. The device of claim 8, wherein the transducer membrane comprises doped silicon having a dopant concentration of $1\times10^{18}$ atoms/cm$^3$ to $1\times10^{19}$ atoms/cm$^3$.

11. The device of claim 7, wherein the bottom cavity layer comprises a layer stack including an $SiO_2$ layer and an aluminum oxide ($Al_2O_3$) layer.

12. The device of claim 7, further comprising a transducer bottom electrode layer disposed beneath the bottom cavity layer.

* * * * *